United States Patent [19]

Yoshizawa et al.

[11] 4,183,807
[45] Jan. 15, 1980

[54] TREATMENT OF WASTE WATER RICH IN NUTRIENTS

[75] Inventors: Kiyoshi Yoshizawa, Tokyo; Kikuo Nojiro, Machida; Katsuyoshi Mitsutomi, Ushiku; Hiroshi Hashimoto, Yachiyo; Akira Noguchi, Urawa; Kazuo Tanno, Tanashi, all of Japan

[73] Assignees: National Tax Administration Agency, Chiyoka; Toho Zinc Co. Ltd., Tokyo; The Hokuren Federation of Agricultural Cooperative Associations, Sapporo, all of Japan

[21] Appl. No.: 941,017

[22] Filed: Sep. 11, 1978

[30] Foreign Application Priority Data

Sep. 12, 1977 [JP] Japan ................................ 52-108758
Aug. 1, 1978 [JP] Japan ................................ 53-93117

[51] Int. Cl.$^2$ ............................ C02C 1/04; C02C 5/10
[52] U.S. Cl. .......................................... 210/2; 210/7
[58] Field of Search ................... 210/2, 11, 7; 195/7, 195/37–41, 4, 14–16

[56] References Cited

U.S. PATENT DOCUMENTS

| | | | |
|---|---|---|---|
| 3,105,014 | 9/1963 | Harrison | 210/2 X |
| 3,660,278 | 5/1972 | Mimura et al. | 210/11 |
| 3,751,338 | 8/1973 | Farris | 210/11 X |
| 3,769,164 | 10/1973 | Azarowicz | 210/11 X |
| 3,801,499 | 4/1974 | Luck | 210/11 |
| 3,943,038 | 3/1976 | Morinaga et al. | 195/37 X |
| 4,094,739 | 6/1978 | Schroeck | 195/7 |

FOREIGN PATENT DOCUMENTS 2506149 8/1976 Fed. Rep. of Germany ............. 195/39

Primary Examiner—Thomas G. Wyse
Attorney, Agent, or Firm—Browdy and Neimark

[57] ABSTRACT

Newly isolated polysaccharide assimilating yeasts are added to a waste water rich in nutrients thereby making such yeasts assimilate nutrients, so that B.O.D. of the waste water is efficiently decreased. Among the polysaccharide assimilating yeasts, ellipsoideus YS-1, FERM-P No. 4498, in particular, can decompose and assimilate sulfurous acid, starch and protein at once, and therefore the B.O.D. of the waste water from starch production plants can be considerably decreased.

3 Claims, No Drawings

TREATMENT OF WASTE WATER RICH IN NUTRIENTS

The present invention relates to a method of treating a waste water rich in nutrients, and more particularly to a method of decreasing the B.O.D. of a waste water comprising treating a waste water from a food production plant containing large quantities of sugars and proteins by use of polysaccharide assimilating yeasts and thereby making said yeasts assimilate the starch and protein.

In general, the waste water from a food production plant contains large quantities of sugars and proteins, and therefore if it is discharged without any treatment, rivers become rich in nutrients resulting in pollution of the rivers.

The inventors of the present invention had researched in a wide range for seeking microbes useful for treating effectively a waste water from food production plants, and as a result the existence of a number of polysaccharide assimilating yeasts were found. It was further discovered that these yeasts were surprisingly effective in the treatment of the waste water of food production. It had also been found that if the waste water of food production treated by said yeasts is further subjected to the treatment with activated sludge, B.O.D. of the waste water can very efficiently be decreased, thus completing the present invention.

The present invention is a method of adding one or more kinds of the polysaccharide assimilating yeasts to the waste water of a food production plant thereby making said yeasts assimilate and consume organic matter and moreover a method of treating the waste water thus treated with activated sludge.

The treating method of waste water according to the present invention is applicable in a very wide range. For example, it is applicable very effectively to the waste water of the production related with food such as waste water of production of alcoholic liquors such as Japanese sake, shochu, wine and beer etc., waste water of production of drink such as fruit juice and refreshing drink etc., waste water of production of yeasts, waste water of bean paste production, waste water of noodle production, waste water of potato starch production, waste water of treatment of fishes and meats, waste water of soybean paste or curd, waste water of paste removing treatment and waste water of dyeing treatment and so forth.

The polysaccharide assimilating yeasts used in the present invention have been newly found by the present inventors in a very wide range, and these yeasts are known strains taxonomically. However, it has not previously been recognized that these yeasts have a polysaccharide assimilating property to decompose and assimilate polysaccharide in waste water, thereby purifying the waste water.

The polysaccharide assimilating yeasts used in the present invention can easily be isolated and collected by a suggestion of the existence of the polysaccharide assimilating yeasts, and therefore they are not limited to a particular kind of strain, but the effective strains of the present invention and their deposition numbers are as follows:

*Debaryomyces hansenii D-N*, FERM-P No. 3592
*Pichia acaciae AM-37W*, FERM-P No. 3593
*Hansenula anomala Y-1*, FERM-P No. 3594
*Pichia nakazawae LKB-335*, FERM-P No. 3595
*Pichia dispora Pd-671*, FERM-P No. 3596
*Candida sp. AS-50*, FERM-P No. 3597
*Endomycopsis platypodis AM-46*, FERM-P No. 3598
*Saccharomycopsis cerevisiae Br-1*, FERM-P No. 3972
*Saccharomyces cerevisiae var. ellipsoideus YS-1*, FERM-P No. 4498

These isolated yeasts are all known microorganisms, and the details of taxonomic studies of these yeasts are shown as follows:

*Debaryomyces hansenii D-N*
Growth in malt extract (25° C., cultivation for two days): Cell is spherical or short-oval. Pellicle and sediment are produced.
Growth on malt agar (17° C., cultivation for one month): Streak culture is yellowish and smooth.
Slide culture: Pseudomycelium is not produced.
Ascospores formation: Usually one spore is formed in the ascus produced by the conjugation of two vegetable cells. One oil drop is formed at the center of the spore.
Glucose fermentation: Weak
Nitrate assimilation: Negative
Vitamin requirement: Positive
Growth at 37° C.: Negative

*Pichia acaciae AM-37W*
Growth in malt extract (25° C., cultivation for two days): Cell is spherical, short-oval or elongate. Sediment is formed.
Growth on malt agar (17° C., cultivation for one month): Streak culture is grayish-brown and wrinkled.
Slide culture: Pseudomycelium is formed. 2–3 or a number of blastospores are branched.
Ascospores formation: Hat-shaped two to four spores having short rim are formed in the ascus produced by the conjugation of two vegetable cells.
Fermentation of sugars: Glucose is fermented.
Assimilation: Nitrate, succinic acid and citric acid are assimilated.
Vitamin requirement: Positive
Growth at 37° C.: Positive

*Hansenula anomala Y-1*
Growth in malt extract (25° C., cultivation for three days): Cell is spherical, oval or elongate. Pellicle and sediment are produced.
Growth on malt agar (17° C., cultivation for one month): Streak culture is grayish-white smooth or dry white and notably wrinkled.
Slide culture: Elongate cells are chained and pseudomycelium is formed. Blastospore is spherical or oval.
Ascospores: Vegetable cell becomes ascus directly, and one to four hat-shaped spores are formed.
Fermentation of sugars: Glucose, sucrose and raffinose (1/3) are fermented. Galactose and maltose are feebly fermented or not fermented at all
Nitrate assimilation: Negative
Vitamin requirement: Negative

*Pichia nakazawae LKB-335*
Growth in malt extract (25° C., cultivation for three days): Cella is oval or cylindrical. Thin pellicle and sediment are produced.
Growth on malt agar (17° C., cultivation for one month): Streak culture is creamy colored and smooth.
Slide culture: Pseudomycelium and blastospores are formed.
Ascospores: After the conjugation, ascus is formed. Hat-shaped two to four spores.

Fermentation: Glucose and galactose are fermented.
Nitrate assimilation: Negative
Vitamin requirement: Negative
Growth at 37° C.: Negative

*Pichia dispora Pd-671*
Growth in malt extract (25° C., cultivation for two days): Cell is spherical or short-oval. Pellicle and sediment are produced.
Growth on malt agar (17° C., cultivation for one month): Streak culture is creamy to brownish and smooth and flat.
Slide culture: Pseudomycelium is not formed.
Ascospores formation: Ascus is formed by sexual generation, and rarely by non-sexual generation (vegetable reproduction). Usually two spherical or oval spores (having a pair of short rims) are formed.
Fermentation: Glucose is fermented.
Assimilation: dl-lactic acid and succinic acid are assimilated but nitrate is not assimilated.
Vitamin requirement: Positive
Growth at 37° C.: Positive

*Candida sp. AS-50*
Ascospores formation: Negative
Growth in malt extract (25° C., cultivation for two days): Cell is spherical or cylindrical.
Slide culture: Pseudomycelium is formed.

*Endomycopsis platypodis AM-46*
Growth in malt extract (25° C., cultivation for two days): Cell is spherical, oval or elongate, and in addition there are pseudomycelium and also true mycelium. Pellicle and sediment are formed.
Growth on malt agar (17° C., cultivation for one month): Streak culture is orange-yellowish, and protruded notably and plaited.
Slide culture: Branch formation of true mycelium and pseudomycelium is abundant. Spherical or oval blastospore is produced at the end of mycelium.
Ascospores formation: Two to four hat-shaped spores are formed in the ascus produced by the conjugation of two vegetable cells and as well as in chained mycelium-like cells.
Glucose fermentation: Weak
Assimilation: dl-lactic acid, succinic acid, citric acid and nitrate are assimilated.
Vitamin requirement: Positive
Growth at 37° C.: Negative

*Saccharomyces cerevisiae Br-1*
Growth in malt extract (25° C., cultivation for two days): Cell is spherical or short-oval. Sediment is produced.
Growth on malt agar (17° C., cultivation for one month): Streak culture is creamy to light brownish-gray.
Ascospores formation: Two to three ascospores are formed.
Fermentation: Glucose, sucrose, maltose, galactose and raffinose (3/1) are fermented.
Vitamin requirement: Positive
Nitrate assimilation: Negative

| Sugar Assimilation | | | | | | | | |
|---|---|---|---|---|---|---|---|---|
| | D.hansenii D-N | P.acaciae Am-37W | H.anomala Y-1 | P.nakazawae LKB-335 | P.dispora Pd-671 | C.species As-50 | E.platypodis Am-46 | S.cereveslae Br-1 |
| Glucose | + | + | + | + | + | + | + | + |
| Sucrose | + | − | + | + | − | + | + | |
| Maltose | ± | + | + | + | − | + | + | + |
| Galactose | + | + | − | + | − | + | ± | + |
| Lactose | ± | − | − | − | − | + | ± | − |
| Melibiose | | − | − | − | | | | + |
| Cellobiose | + | + | + | + | − | + | + | + |
| D-Ribose | + | + | − | − | − | + | + | + |
| Raffinose | + | − | + | − | − | + | + | + |
| D-Xylose | + | + | + | + | − | + | + | + |
| L-Arabinose | + | − | + | + | − | + | + | + |
| α-methyl glucoside | ± | + | + | + | − | + | + | + |
| Salicin | − | + | + | + | − | + | + | − |
| Inulin | + | − | − | − | − | + | + | + |
| Cellulose | + | | | | | + | ± | |
| Soluble starch | + | + | + | + | − | + | + | + |
| D-Mannitol | ± | + | + | + | + | + | + | + |
| Sorbitol | ± | + | + | | + | + | + | |
| Ethanol | ± | + | + | + | + | + | + | + |
| Glycerol | ± | + | + | + | − | + | + | + |
| | | | | | | | Trehalose | + |

*Saccharomyces cerevisiae var. ellipsoideus YS-1*

This mutant strain has substantially the same microbial properties as those of *Saccharomyces cerevisiae var. ellipsoideus*, and the various properties thereof are as described in "The Yeasts, a taxonomic study 2nd edition" (by J. Lodder, 1970) pages 562 and 596, and its outline is as follows:

It is generated by the multilateral budding. Cell is generally of oval shape. Pseudomycelium is formed. Four ascospores are formed. Pellicle is not formed. Nitrate is not assimilated, and arbutin is not decomposed.

| Sugar assimilation (Fermentation) | | | |
|---|---|---|---|
| Glucose | +(+) | Lactose | −(−) |
| Galactose | +(+) | Raffinose | +(+) |
| Sucrose | +(+) | Arabinose | + |
| Maltose | +(+) | | |

This mutant has a specific property of sulfurous acid tolerance. Next, with respect to the present mutant strain and, as a comparison, the two species *Saccharomyces cerevisiae Br-1*, FERM-P No. 3972 and *Saccharomyces cerevisiae K7*, ATCC No. 26422, the measurement of the yeast cell count of each strain was carried out at various increasing concentrations $SO_2$. Each strain was propagated in the clarifier waste water of potato starch to which were added varying amounts of sulfurous acid. Thus the yeast cell count was measured at each $SO_2$ concentration. The results are shown in the following table. In this case, C.O.D. of the waste water was 17,460 ppm, and each strain was inoculated at inoculum size of $10^6$ cells/ml of the waste water and cultured at 30° C. for 45 hrs.

| | Number of grown cell (cells/ml) | | |
|---|---|---|---|
| $SO_2$ ppm | YS-1 FERM-P No. 4498 | Br-1 FERM-P No. 3972 | K7 ATCC No. 26422 |
| 20 | $3.0 \times 10^8$ | $2.0 \times 10^8$ | $2.0 \times 10^8$ |
| 100 | $3.0 \times 10^8$ | $1.0 \times 10^8$ | $4.5 \times 10^6$ |
| 300 | $2.8 \times 10^8$ | $5.0 \times 10^7$ | Trace |
| 540 | $2.2 \times 10^7$ | $2.5 \times 10^6$ | Trace |
| 800 | $2.0 \times 10^7$ | Trace | Trace |
| 920 | $2.1 \times 10^7$ | Trace | Trace |

As is obvious from the table above, the present strain YS-1 is sufficiently able to be propagating even in the presence of above 800 ppm of sulfurous acid.

Moreover, the present strain is such a specific strain that continues its propagation in the acidified range with sulfurous acid and at the same time assimilates the acid and the nourishments. Next, with respect to the present strain and, as a comparison, the two species Saccharomyces cerevisiae Br-1, FERM-P No. 3972 and Saccharomyces cerevisiae K7, ATCC No. 26422, each strain was inoculated at inoculum size of $10^8$/ml of the clarifier waste water of potato starch (C.O.D. 20,800 ppm, $SO_2$ 300 ppm, pH 5.0), and then each strain was incubated with shaking at 30° C. for 40 hrs. The results are shown in the following table, and it is seen that only the present strain can assimilate the acid and simultaneously can assimilate the starch and decrease C.O.D.

| | Results after 40 hrs. culture | | | |
|---|---|---|---|---|
| | DH | COD (ppm) | Remained $SO_2$ (ppm) | Number of cell ($\times 10^8$/ml) |
| YS-1, FERM-P No. 4498 | 7.9 | 3,100 | 25 | 2.2 |
| Br-1, FERM-P No. 3972 | 5.0 | 15,000 | 50 | 0.6 |
| K7, ATCC No. 26422 | 5.0 | 18,000 | 60 | 0.3 |

The waste water treatment according to the present invention is carried out by adding the incubation mixture of each strain to the waste water rich in nutrients itself or the waste water subjected to a pretreatment such as filtration, centrifugal separation or chemical treatment, etc. As the incubation mixture, such one that was cultured from a seed culture in large quantities may be used, and also the cells cultured by the treatment of waste water in large quantities may be returned to be used. The inoculum size is preferably about $10^5$–$10^7$ cells/ml, but it may be varied according to the length of the period of cultivation.

The temperature of cultivation is preferably about 20°–35° C., but even if below 20° C. it is possible to perform the waste water treatment in case that the cultivation is carried out for a longer time. The cultivation is carried out under the aerobic conditions such as stirring, ventilation and so forth.

In the treatment of the present invention, if necessary, as a nutrient, sources of phosphorus or sources of nitrogen, for example ammonium chloride etc. may be added to the waste water.

In the case when the inoculum size of the cells is low, the growth of yeast requires about two days if the waste water to be treated has a C.O.D. below several hundred ppm; however, in the case when the inoculum size of the cells is sufficient, the treatment may be complete within one day if the C.O.D. of the waste water is above 500 ppm.

The removal rate of C.O.D. by the removal of yeast is generally between 90 and 95%. For example, it is possible to obtain a treated water of a C.O.D. of about 70 ppm by treating a waste water to be treated of a C.O.D. of 750 ppm from which suspended solid has been removed.

The waste water obtained by the treatment of a waste water rich in nutrients by use of the strain of the present invention is fed to an activated sludge treating tank as it is or after it has appropriately been mixed with a waste water, etc., having a decreased C.O.D., so that it may be more effectively removed of C.O.D. In this case, it is also possible to separate the cells existing in the waste water in large quantities, but it is also convenient, from the viewpoint of the operation of waste water treatment, that the waste water be directly fed into the activated sludge tank as it is without specially separating the cells, and as well the yeasts fed into the activated sludge tank become the nutrient of the activated sludge especially protozoa thereby resulting in increasing the activity of the sludge. Furthermore the removal of sludge from the bed does not occur and therefore such waste water is very advantageous for the activated sludge treatment.

As the activated sludge treating tank, it is possible to use any types usually used, such as a lagoon, a trickling filter process and so forth; however, one which is convenient for the use is an activated sludge treating tank in which a bed such as honeycomb, etc., is applied with the activated sludge.

The activated sludge treatment is carried out in such a way that the waste water is ventilated by means of an air sprayer while the cells being contained therein and circulated through the activated sludge zone are applied to a fixed bed. The circulation dwelling time is sufficiently about 10 to 30 hours.

As a result of this treatment, a C.O.D. of about 1,000 ppm (including the yeast cells) of the waste water to be treated is reduced to about 20 to 50 ppm (after the microbes have naturally been sedimented). In this case, it is also possible to separate forcibly the microbes by coagulation precipitation using an coagulating agent, centrifugal separation by means of a centrifugal separator and so force separation without allowing natural sedimentation.

As a treatment of coagulation precipitation by the use of a coagulating agent, a coagulation process is effective in which for example ferric chloride, polyaluminum chloride and polyacrylamide are used jointly.

In this coagulation process, the waste water to be treated containing the cells is added with ferric chloride while it is stirred. Due to this addition treatment, the pH decreases, and therefore the pH is regulated to a pH of between 6.5 and 7.5, preferably 7.0, by the use of an alkaline solution such as caustic soda solution etc. Such a pH value is required for the formation of huge floc. With the increase of iron ion, the remaining amount of C.O.D. decreases. However, the addition of iron in large quantities is not economical and results in the remaining of iron ion in the treated liquid, so that this treatment is not desirable. Accordingly, preferably it is necessary an addition corresponding to a concentration of between 100 and 300 ppm by ferric ion. Under the condition of the pH adjustment as described above, 10% solution of polyaluminum chloride is added to the waste water in an amount of between about 200 and 300 ml per 1m³ of waste water, and moreover about 10 ppm of polyacrylamide is added thereto thereby making floc huge. The constant speed sedimentation velocity of the produced floc is as large as 5-6m/hr. and accordingly the separation and removal of the floc by the coagulation precipitation is sufficiently possible. The obtained precipitate can be easily separated off by filtration.

The final C.O.D. of the waste water becomes 5-30 ppm, and such a waste water can be discharged as it is without any treatment.

Moreover, after the yeast treatment, the yeasts are subsequently separated from the treated water by a method such as centrifugal separation, and the obtained cells can be utilized for animal feed and so forth.

Hereinafter, experimental examples will be shown.

EXPERIMENTAL EXAMPLE 1

Each 250 ml of the waste water of potato starch production (liquid of the clarifier waste water diluted 2 times), pH=6.27, C.O.D. 4,700 ppm, was put in each 500 ml beaker.

On the other hand, each 50 ml of the koji extract medium was respectively inoculated with one platinum loop of the strain, and the preculture was carried out by incubating it with shaking at 30° C. for 16 hours, and after the end of the preculture, the cells were centrifugally separated, and the obtained cells were washed by adding with physiological saline solution thereby preparing inoculation cells.

Each flask prepared above was inoculated with these cells, and incubated under aeration, and the resulting treated liquid is subjected to centrifugal separation at 3,000 G, and the supernatant liquid was collected, and each C.O.D. of such liquid samples was measured and each C.O.D. removal rate was obtained. The results are shown in the following table.

Table

| Experimental Number | Strain | Cell count | C.O.D. (ppm) | C.O.D. Removal Rate(%) |
|---|---|---|---|---|
| 1 | Pichia acaciae AM-37W | 2.50 + 10⁸ | 420 | 91.1 |
| 2 | Hansenula anomala Y-1 | 2.80 + 10⁸ | 205 | 95.6 |
| 3 | Candida sp. AS-50 | 3.60 + 10⁸ | 326 | 93.1 |
| 4 | Endomycopsis Platypodis AM-46 | 3 + 10⁵ | 400 | 91.5 |
| 5 | Control | — | 2905 | 38.2 |

EXPERIMENTAL EXAMPLE 2

Each waste water of the experimental numbers 1 to 5 treated in Experimental example 1 was treated with activated sludge (MLSS 3,000 ppm) for a dwelling time of 72 hours under the aeration conditions of 0.5 l/min, and thereafter it was introduced into a precipitation tank and allowed to stand therein for 3 hours and thereafter C.O.D. (ppm) of the supernatant liquid was measured.

The results thereof are shown in the following table.

Table

| Experimental Number | Experimental Number of Example 1 | C.O.D. at the Time of Flowing-in (ppm) | C.O.D. of the Supernatant Liquid (ppm) |
|---|---|---|---|
| 6 | 1 | 420 | 40 |
| 7 | 2 | 205 | 15 |
| 8 | 3 | 326 | 18 |
| 9 | 4 | 400 | 45 |
| 10 | 5 | 2905 | 627 |

EXPERIMENTAL EXAMPLE 3

Various inoculation cells were prepared in the same manner as Experimental example 1.

Each 250 ml of the waste water of soybean curd production having C.O.D. 1,250 ppm and total sugars of 800 ppm was put in each 500 ml beaker, and each beaker was inoculated with inoculation cells, and incubated under aeration at 30° C. for 48 hours, and the resulting treated liquid was subjected to centrifugal separation at 3,000 G, and the supernatant liquid was collected, and each C.O.D. of such liquid samples was measured and each C.O.D. removal rate was obtained. The results are shown in the following table.

Table

| Experimental Number | Strain | C.O.D. (ppm) | C.O.D. Removal Rate (%) |
|---|---|---|---|
| 11 | Debaryomyces hansenii D-N | 150 | 88.0 |
| 12 | Pichia acaciae AM-37W | 144 | 88.5 |
| 13 | Hansenula anomala Y-1 | 171 | 86.3 |
| 14 | Pichia dispora Pd-671 | 167 | 86.4 |
| 15 | Candida sp. AS-50 | 86 | 93.1 |
| 16 | Endomycopsis platypodis Am46 | 95 | 92.4 |
| 17 | Control (no addition of strain) | 957 | 23.4 |

EXPERIMENTAL EXAMPLE 4

Each waste water of the experimental numbers 11 to 17 treated in Experimental example 3 was added with the activated sludge (MLSS 3,000 ppm), and treated for 24 hours while aerating at the rate of 0.5 l/min. by means of an air sprayer, and then the treated liquid was introduced into a precipitation tank and allowed to stand therein for three hours as it was, and thereafter C.O.D. (ppm) of the supernatant liquid was measured.

The results thereof are shown in the following table.

Table

| Experimental Number | Experimental Number of Example 3 | C.O.D. at the Time of Floowing-in (ppm) | C.O.D. of the Supernatant Liquid (ppm) |
|---|---|---|---|
| 18 | 11 | 150 | 25 |
| 19 | 12 | 144 | 22 |
| 20 | 13 | 171 | 35 |
| 21 | 14 | 167 | 30 |
| 22 | 15 | 86 | 20 |
| 23 | 16 | 95 | 18 |
| 24 | 17 | 957 | 601 |

EXPERIMENTAL EXAMPLE 5

200 ml of the waste water of potato starch production (C.O.D. 20,800 ppm, $SO_2$ 300 ppm, pH=5.0) was put in a 500 ml flask.

On the other hand, each 50 ml of koji extract medium was respectively inoculated with one platinum loop of *Saccharomyces cerevisiae var. ellipsoideus* YS-1, FERM-P No. 4498 and the preculture was respectively carried out by incubating it with shaking at 30° C. for 16 hours, and after the end of the preculture the cells were centrifugally separated, and the obtained cells were washed by adding with physiological saline solution thereby preparing inoculation cells.

Each flask prepared above was inoculated with these cells in such an amount that the count of cells was $10^7$ cells/ml, and incubated under aeration conditions at 30° C. for 40 hours. C.O.D. (ppm), total N (ppm) and total sugars (ppm) were respectively measured before and after culture and the removal rate (%) was determined.

The results are shown in the following table.

In this case, 9 g/l of the dry cells was yielded.

Table

|  | Before Treatment | After Treatment | Removal Rate (%) |
|---|---|---|---|
| C.O.D. ppm | 11,460 | 2,540 | 85.5 |
| Total N ppm | 1,600 | 396 | 75.3 |
| Total Sugars ppm | 13,200 | 1,000 | 92.4 |

EXPERIMENTAL EXAMPLE 6

The waste water of potato starch production was allowed to stand for 24 hours as it was, and after the sedimentation of the starch, the upper liquid was regulated to pH=4.5 and subjected to centrifugal separation at 1,000 G for 5 min. to obtain the supernatant liquid (C.O.D. 14,5000 ppm), and said liquid was respectively inoculated with following cells described below in the same manner as Experimental example 1 such that the number of cells is $10^7$ cells/ml, and cultivated at 30° C. for 40 hours, and pH, C.O.D. (ppm) and the number of cells after the cultivation were measured.

1. *Saccharomyces cerevisiae var. ellipsoideus* YS-1, No. 4498
2. *Saccharomyces cerevisiae* K7, ATCC No. 26422
3. *Hansenula anomala* Y-1, FERM-P No. 3594
4. *Endomycopsis platypodis* AM-46, FERM-P No. 3598
5. *Candida sp.* AS-50, FERM-P No. 3597

The results are shown in the following table.

Table

| Used Strain | pH | C.O.D. (ppm) | Cell Count ($\times 10^8$/ml) |
|---|---|---|---|
| 1 | 7.7 | 2,020 | 2.0 |
| 2 | 4.8 | 10,100 | 0.3 |
| 3 | 7.7 | 3,710 | 1.7 |
| 4 | 7.7 | 4,410 | 1.2 |
| 5 | 7.9 | 3,510 | 1.2 |
| Control | 4.7 | 13,100 | — |

Next, practical examples of the present invention will be shown.

PRACTICAL EXAMPLE 1

Treatment tank containing 1.5 l of the waste water of potato starch production (clarifier waste water: C.O.D. 20,800 ppm) was inoculated with $10^7$ cells of *Saccharomyces cervisiae var. ellipsoideus* YS-1, FERM-P No. 4498 per 1 ml of said waste water, and after the cultivation the waste water was added into the tank at a rate of 1 ml/min., and the content of the tank was stirred at a temperature of 24°–25° C. while the overflowed waste water treated in the tank for the dwelling time of 24 hours was continuously added into the subsequent activated sludge treating tank. In the tank the said treated water was stirred with aeration for a dwelling time of 72 hours, and then the treated waste water was subjected to the natural sedimentation thereby separating the yeasts.

The supernatant liquid was discharged, but due to the continuous treatment for 12 days C.O.D. of the treated water was 17–19 ppm.

PRACTICAL EXAMPLE 2

Each 19 l of the waste water (C.O.D. about 500 ppm) resulting from the mixing of the rice washing waste water and the Sake tank washing waste water in a C.O.D. ratio of 5:3 according to the practice of a Saké brewing factory was inoculated respectively with *Pichia acaciae* AM-37W, FERM-P No. 3593 and *Hansenula anomale* Y-1, FERM-P No. 3594 each at an inoculum size of $10^7$ cells/ml individually, and after the cultivation the waste water was added into said cultivated waste waters at a rate of 10.8 ml/min. respectively, and while stirring at 24°–25° C., the treating waste water overflow after the dwelling time of 28 hours was added continuously into the subsequent activated sludge treating tank.

The activated sludge treating tank is provided with a honeycomb bed (volume 3,820 $cm^3$, surface area 0.68 $m^2$) which is applied with the activated sludge, and in which tank 9.5 l of the waste water is circulated through said honeycomb bed while aerating at a rate of 4 l/min. by means of an air sprayer.

In this embodiment, two of such treating tanks were provided, and the waste water were circulated through the two tanks with a dwelling time of 28 hours, and the treated waste water was introduced into a sedimentation tank (volume 3 l) or a coagulation precipitating tank thereby separating the cells by the natural sedimentation or coagulating precipitation.

In the case of the coagulating precipitation, polyaluminum chloride (60 ppm) and polyacrylamide (5 ppm) were added and pH was adjusted to 7–7.5 and thus the coagulation treatment was carried out. The obtained results are shown in Table 1 and Table 2.

As is evident from the Tables 1 and 2, C.O.D. of the discharged waste water was decreased to about 9–29 ppm thus resulting in a good result.

Table 1

| | Discharged Waste Water *Pichia acaciae* AN-37W | | | | | |
|---|---|---|---|---|---|---|
| | Original Water | | Treated Water Natural Precipitation[1] | | Coagulating | |
| Passed Days | C.O.D. ppm | pH | C.O.D. ppm | pH | C.O.D. ppm | pH |
| 1 | 586 | | 68[2] | | 26 | 7.0 |
| 2 | 360 | | 61 | | 29 | 7.0 |
| 3 | 477 | | 66 | 7.7 | 25 | 7.0 |
| 4 | 432 | | 58 | 7.7 | 15 | 7.0 |
| 5 | 468 | 6.7 | 67 | 7.6 | 13 | 7.0 |
| 6 | 492 | 6.4 | 56 | 7.5 | 11 | 7.0 |
| 7 | 540 | 6.4 | 45 | 7.4 | 12 | 7.0 |
| 8 | 480 | 6.3 | 28 | 7.6 | 11 | 7.0 |
| 9 | 594[3] | 6.7 | 30 | 7.6 | 10 | 7.0 |

Table 2

Discharged Waste Water
*Mansenula anomala Y-1*

| | Original Water | | Treated Water Natural Sedimentation | | Coagulating Precipitation (1) | |
|---|---|---|---|---|---|---|
| Passed Days | C.O.D. ppm | pH | C.O.D. ppm | pH | C.O.D. ppm | pH |
| 1 | 586 | | 65(2) | | 25 | 7.0 |
| 2 | 360 | | 46 | | 29 | 7.0 |
| 3 | 477 | | 49 | 7.6 | 21 | 7.0 |
| 4 | 432 | | 62 | 7.7 | 17 | 7.0 |
| 5 | 468 | 6.7 | 61 | 7.6 | 11 | 7.0 |
| 6 | 492 | 6.4 | 56 | 7.5 | 11 | 7.0 |
| 7 | 540 | 6.4 | 41 | 7.5 | 14 | 7.0 |
| 8 | 480 | 6.3 | 26 | 7.5 | 9 | 7.0 |
| 9 | 594 | 6.7 | 27 | 7.5 | 12 | 7.0 |

In Table 1 and Table 2;

(1) Polyaluminum chloride 60 ppm and Polyacrylamide (Akofloc A-110) 5 ppm were used.

(2) Value after the lapse of 15 hours from the flowing-in (3) SS 470 ppm (4) Temperatures were all room temperature.

What is claimed is:

1. A method of treating waste water rich in nutrients, comprising:

adding to a waste water rich in nutrients a polysaccharide assimilating yeast selected from the group consisting of

*Debaryomyces hansenii D-N*, FERM-P No. 3592,
*Pichia acaciae AM-37W*, FERM-P No. 3593,
*Hansenula anomala Y*-1, FERM-P No. 3594,
*Pichia nakazawae LKB*-335, FERM-P No. 3595,
*Pichia dispora Pd*-671, FERM-P No. 3596,
*Candida sp. As*-50, FERM-P No. 3597,
*Endomycopsis platypodis AM*-46, FERM-P No. 3598,
*Saccharomyces cerevisiae BR*-1, FERM-P No. 3972, and
*Saccharomyces cerevisiae var. ellipsoideus YS*-1, FERM-P No. 4498 thereby making said yeast assimilate the nutrients in the waste water; and flowing the obtained waste water into an activated sludge tank in which the obtained waste water is treated with an activated sludge.

2. A method in accordance with claim 1, further including the step of, after said adding step and prior to said flowing step, substantially separating the yeast from the obtained waste water.

3. A method of treating waste water of starch production comprising adding *Saccharomyces cerevisiae var. ellipsoideus YS*-1, FERM-P No. 4498 to a waste water of starch production thereby causing sulfurous acid to be decomposed and starch and protein to be assimilated, and flowing the resulting treated waste water down into an activated sludge tank in which said treated waste water is treated with an activated sludge.

* * * * *